United States Patent [19]

Adachi et al.

[11] Patent Number: 4,692,003
[45] Date of Patent: Sep. 8, 1987

[54] REAL-TIME ANALYSIS KERATOMETER

[76] Inventors: Iwao P. Adachi; Yoshifumi Adachi, both of 15042 Temple St., Westminster, Calif. 92683; Robert E. Frazer, 317 San Juan Way, La Canada, Calif. 91011

[21] Appl. No.: 549,157

[22] Filed: Nov. 7, 1983

[51] Int. Cl.[4] ............................................. A61B 3/10
[52] U.S. Cl. ................................................. 351/212
[58] Field of Search ........................ 351/211, 212, 247

[56] References Cited

U.S. PATENT DOCUMENTS 3,248,162  4/1966  Knoll .................................. 351/212

Primary Examiner—Rodney B. Bovernick
Attorney, Agent, or Firm—James T. English

[57] ABSTRACT

A computer assisted keratometer in which a fiducial line pattern reticle illuminated by CW or pulsed laser light is projected on a corneal surface through lenses, a prismoidal beamsplitter quarterwave plate, and objective optics. The reticle surface is curved as a conjugate of an ideal corneal curvature. The fiducial image reflected from the cornea undergoes a polarization shift through the quarterwave plate and beamsplitter whereby the projected and reflected beams are separated and directed orthogonally. The reflected beam fiducial pattern forms a moire pattern with a replica of the first recticle. This moire pattern contains transverse aberration due to differences in curvature between the cornea and the ideal corneal curvature. The moire pattern is analyzed in real time by computer which displays either the CW moire pattern or a pulsed mode analysis of the transverse aberration of the cornea under observation, in real time. With the eye focused on a plurality of fixation points in succession, a survey of the entire corneal topography is made and a contour map or three dimensional plot of the cornea can be made as a computer readout in addition to corneal radius and refractive power analysis.

10 Claims, 5 Drawing Figures

MEASURED −STD = CORNEA

REAL-TIME ANALYSIS KERATOMETER

ORIGIN OF THE INVENTION

This invention was made with Government support under NAS7-918 awarded by NASA. The Government has certain rights in the invention.

TECHNICAL FIELD

The invention relates to keratometers used in Opthalmologic diagnosis and measurement of the corneal curvature and topography of the eye, by means of a circular grating moire method. These topographic data are displayed and printed out in real-time; i.e., instantly. Measurements of corneal diameter may exceed 9 mm for a typical cornea of radius 7.5 mm. The limbus is also measured with a typical radius of 12.5 mm. These measurements are made at the present time by standard keratometry, which measures the radius along a chord length measuring 3 mm over the central region of the cornea. Photokeratoscopy is also currently available using the corneascope with Placido's circle. These produce photographs of 55% of the corneal surface, for subsequent analysis and evaluation.

Another moire technique projects a linear grating with shorter wavelength (blue) light. The cornea surface is coated with fluorescent liquid, thus a self luminous (fluorescent) grating is temporarily made on the cornea. This image is relayed by a lens, onto another similar grating located so as to form fringes from which topography is deduced. It will be noted that these three methodologies do not occur in real-time. Real-time analysis requires computer processing of digitized keratoscopic data as in the present invention.

DESCRIPTION OF THE PRIOR ART

The Corneascope is a device in widespread use at present for recording corneal topography. A photograph is made of the eye including reflections on the outer surface of the cornea. In operation, a photograph is made of the eye including reflections from a set of illuminated rings presented to the visual field on the interior surface of a sphere. The arrangement is such that a perfectly spherical cornea positioned so that its center of curvature is coincident with the axis of the Placidosphere light sources, will present as reflections, a set of equally spaced concentric circles. Thus for abnormal corneas, departure from circularity and variation in spacing among the reflections can convey information about the corneal topography. The photographs may be compared on a companion optical-mechanical instrument, the Comparator to extract numerical estimates of corneal radius of curvature or refractive power at various locations. Among the limitations of this pair of instruments are: inacessibility of some sections of the cornea including the central region, to detailed examination since the photographic optics penetrate the Placidosphere on axis; there is limited resolution inherent in a fixed set of discrete rings as a light source and uncertainty in the positioning of the center of the Placidosphere light source with respect to the cornea's supposed symmetry. The major drawback, however, is the labor intensive nature of the analysis, its slowness, and its susceptability to operator bias and error. Also, in comparing photographs made on different corneascopes, sensitivity to differences in magnification, and optical distortion, is a problem.

The moire technique has been utilized to measure corneal contour, but images are poor because the cornea is not a scattering surface. A fluorescent liquid can be applied to the cornea so that a grating imaged in blue light on its surface produces a fluorescent emitting grating image. This image is relayed by a lens, to a focus where a grating of corresponding period is arranged to give moire. This moire image is photographed and recorded for data reduction to yield the topography of the cornea. The moire pattern technology is generally described in the following publications: J. J. Rowsey, A. E. Reynods, Randy Brown, "The Archives of Opthalmology 99, 1093", 81, Department of Opthalmology, University of Okla., and: M. Idesawa, T. Yatagai, and T. Soma, Applied Optics, 16, 2152, '77; also, Manuel Malacara, Optical Shop Testing, Wiley, 1977.

BRIEF DESCRIPTION OF THE INVENTION

The novel keratometer is designed to measure a large area of cornea as well as limbus-contour. Mean radius of the cornea may be 7.5 mm, while that of the eye ball is about 12.5 mm. The limbus diameter is 12 mm, thus, the numerical aperture (NA) must be $(12/2) \times (1/12.5) = 0.48$. However, 0.6 is used for the NA, the lens diameter to cover $2 \times NA \times (r$ of cornea$) = 2 \times 0.6 \times 7.5 = 9$ mm.

If the eye fixation point: i.e., the point on which the eye is made to focus, is placed off-center, the area of the eye that is measured can be extended to 14 mm diameter. Fixation spots are optically placed about the center axis (rotated) and the patient is told to redirect the line of sight to each point in turn.

The conditions for measurement are subject to the following constraints: (1) The cornea is a specular steep convex aspherical surface which deviates from a spherical surface by 70 to 100 micrometers, (2) The cornea must be mapped without using fluorescence or self illuminance, (3) The cornea is a low (4%) reflectance surface, but illumination must be limited to avoid damage to the eye, (4) the eye is a dynamic object, moving continuously.

The basic method of this invention to meet these constraints is: (1) Use a moire technique in projecting a circular grating centered normal to the cornea surface, and return the reflection to the conjugate of the original grating to detect the moire pattern, (2) Use a diode laser typically of 830 nanometers wavelength, in the continuous wave mode (CW) for preadjusting; they operate in the pulsed mode at higher power to take data in real-time, (3) Use a CCD camera to accept the moire image and transmit the information to a small computer for data analysis, and (4) Provide a TV monitor to display the moire of the cornea and the topographic data after real-time analysis.

For modern clinical use, the keratometer should operate in real-time and provide both video display and numerical recording capabilities for corneal transplant surgery, and for radial keratotomy surgery, as well as for contact lens fitting. The real-time display such as a television monitor is desired for qualitative observation. When quantitative data from the moving cornea is needed, the cornea is illuminated by pulsed infrared laser light. The continuous CW mode is used for prior adjustment of the apparatus and preliminary observation. In operation, once the measurement parameters are set up, using the CW mode, the system is then switched over to the automatic pulsed data processing mode for pulsed scan and readout through the computer.

The optical arrangement of the invention features a lens system of large numerical aperture and well corrected spherical aberration. In operation, a moire grating, having high spatial frequency, is projected onto the cornea by the laser and the optical system. The area of the cornea which it is desired to measure is 12 millimeters in diameter, and the distance between the last surface of the lens to the cornea should be more than 12.5 millimeters. The optical arrangement is symmetrical in that the reticle grating is located at the conjugate point of the cornea. The illuminating infrared beam is linearly polarized. The polarization of the return beam reflected from the cornea is rotated 90 degrees by means of the combination of a polarizing beam splitter and a quarter wave plate, so that all of the reflected beam is directed to the second grating. A coherent fiber plate for moire fringe detection cuts off the high frequency moire image to the camera.

The beam has a large diverging angle which can be bent toward the optical axis by the fiber optics. This enables very compact moire pattern observing optics.

Another novel feature of the invention is the illumination optics which are designed to correct the Gaussian intensity distribution of the laser. The laser beam, having a Gausian intensity profile, brighter at the central area and falling off in a bell shaped curve toward the edges, can be expressed by: $I_o x e^{-x^2}$; where $I_o$ is the center intensity, x is the coordinate perpendicular to the propagation, a defines the size of the beams, and e is the base of the natural logarithms. Optics based on this formula have been designed to compensate for this uneven distribution to present a uniform beam intensity and wavefront.

BRIEF DESCRIPTION OF THE DRAWINGS

The invention will best be understood by reading the following description with reference to the drawings of which.

DETAILED DESCRIPTION OF THE EMBODIMENTS

Figure 1:
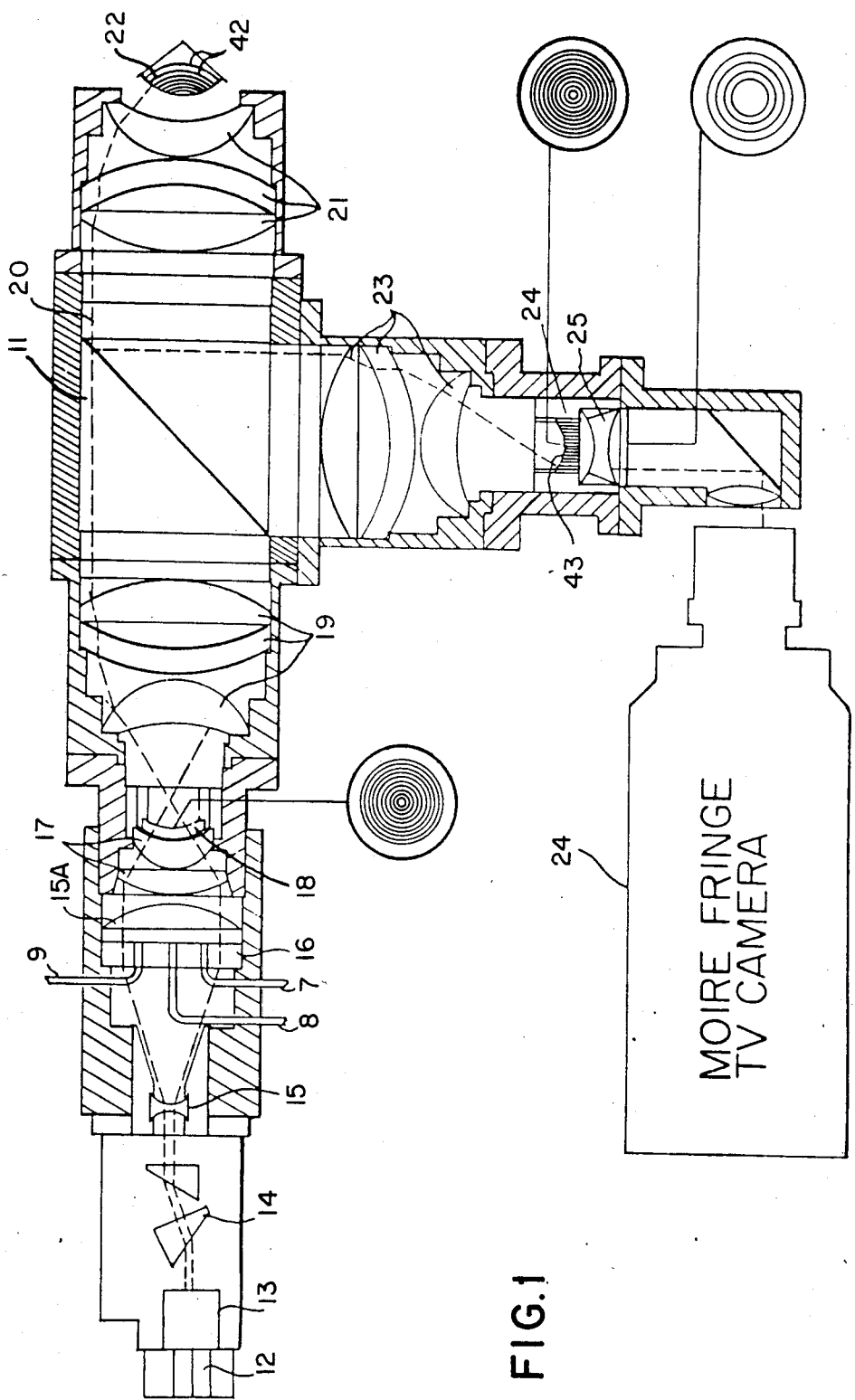
FIG. 1 is an Optical System layout particularly pointing out the conjugate reticles.

Reference is directed to FIG. 1. This figure shows basically a symmetrical optical system on each side of a prismoidal beam splitter 11. The 'beam splitter' 11 passes only polarized light TM mode. Light from the diode laser 12 passes through the collimating lens 13, the beam shaping prism 14, beam expander 15, 15A eye fixation plane 16, condenser lens 17, circular grating 18, then to main collimating lens 19, which forms a quasi-perfect collimated polarized beam. The beam splitter 11 having a multilayer polarizing coating efficiently transmits the TM polarized beam only. A quarter wave plate 20 converts the plane polarized beam to circular polarization. Converging lens 21 directs the beam to the center of curvature of the subject's cornea or other specular reflecting surface.

Because the beam strikes the surface at nearly 0 degree incident angle, if the surface deviates from spherical, the reflected beam does not return along the same path. There will be a shift of direction for the returning beam. In passing through the quarter wave plate 20, the circularly polarized beam is converted back to linearly polarized, but 90 degrees rotated. Now that the vibration domain is rotated 90 degrees, it is in the TE mode. The beam splitter 11 reflects TE mode efficiently and there is no TM mode to pass the beam splitter and reflect back to the original light source to cause "back talk".

Thus, without loss of light, except that lost by reflection of 4% at cornea surface 22, the beam will be collected by converging lens 23 which is identical to collimating lens 19, and 21 so that perfect symmetry of the optical system is maintained. The lens images the modulation caused by surface defects of 22, which is carried across from circular grating 18, to second circular grating 24.

The fiber plate 24, where the modulated circular grating is sharply imaged, has its receiving surface 43 identical to circular grating 18. Thus moire fringes are formed at this surface 43.

It should be mentioned that the quality of these optics has to be near perfect, so that the fine structure of the circular grating 18 will be transferred through without any degradation of contrast, and correctly carries the modulated information imposed by surface 22. The system must be very carefully designed and constructed.

A fiber-optical light guide 8, FIG. 1, produces a spot of light to provide a fixation point. A plurality of these fixation points; Eg. 7 & 9, are arranged around the axis every forty five degrees. These are illuminated, in turn, to aid the patient in directing his line of sight so that larger areas of the eye can be analyzed than if the eye remained focused at the central axis of symmetry.

Once the moire fringe is formed, the high frequency structure of the circular grating is no longer useful. It should be rejected to avoid confusion in the moire analysis. The fiber optic plate 24, and any modification to its surfaces acts as a low pass filter to reject unwanted noise and transmit only the moire fringe pattern. Another important feature of fiber plate 24 is to redirect the beam toward the optical axis for convenience in observation. Without this fiber plate, the beam would propagate with a large numerical aperture, and require a large diameter observing system.

Figure 3:
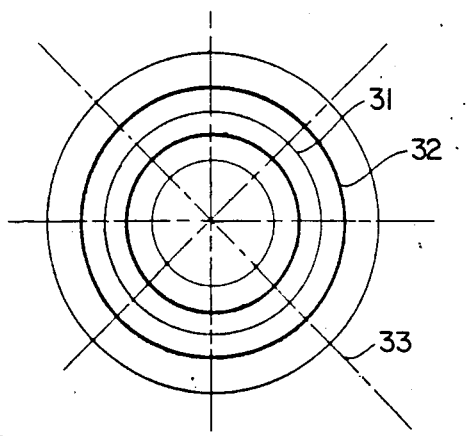
FIG. 3 shows a calculated moire fringe from a spherical cornea.

When circular gratings of 10 per mm are used for the first reticle 18, and second reticle 24, and the cornea is a perfect sphere of 7.5 mm radius, calculated moire fringes are depicted as in FIG. 3. This fringe shows transverse aberration. Every ½ period of the grating constant dark and bright rings 31,32, appear, if the system is concentric. This is confirmed by tests with a ball bearing. This fringe pattern is due to residual spherical aberration in the system and is considered to be a known instrument error which will be removed by the computer during data analysis.

If the cornea surface deviates from a sphere, the location and number of moire fringes varies. The difference is measured as a change of transverse aberration due to asphericity of the corneal surface. The analysis is conducted along an azimuth; e.g., 33, from center out, and the computer analysis converts it to radius and power. When one azimuth is completed, the analysis proceeds to the next azimuth. Measurement of 8 azimuths is sufficient to define the topography of the cornea. Topography of the entire eye is by fixation pts.

Figure 2:
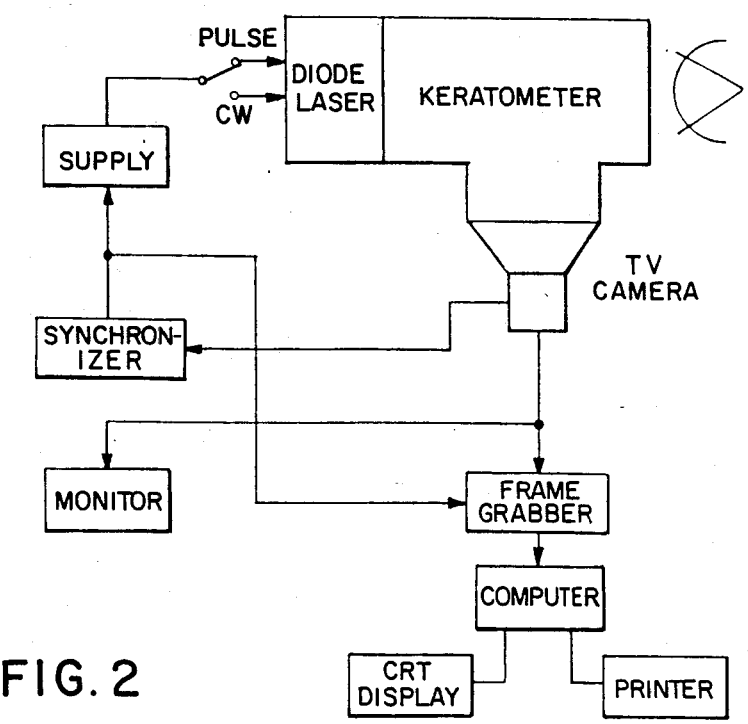
FIG. 2 is the system block diagram.

Referring to FIG. 2 when quantitative data is needed, the system is operated in the pulsed mode and the displayed moire pattern is digitized and stored in a computer memory. To further explain the data transfer in the CW mode, it is pointed out that commercial TV cameras, whether vidicon tube type, charge coupled device (CCD) or MOS solid state cameras, raster scanning of one full frame in 1/30 second takes place. Within the camera, each frame of information is converted to a continuous analog signal with appropriate vertical and horizontal synchronizing pulses. To feed the television information into a computer, the signal must be converted to a group of discrete digital information bits. If for example, 240×320 pixel resolution is needed to define a full field moire pattern, the analog signal must be A/D converted at a rate of 240×320×30, 8-bit pixels (256 grey levels) per second or 2.3 megapixels per second or 18.4 megabits per second. In addition, this information must be stored in a memory at the same speed as the analog to digital conversion rate. A state of the art desktop computer does not have such a fast transfer rate. Typical computers rate their maximum transfer speed at 1 to 1.4 megabits per second. To fill the gap between the television camera and the computer, a frame grabber is needed. This instrument is a high speed A/D converter and memory buffer. The frame grabber digitizes the signal at a high rate and transfers the data to the computer at a lower rate acceptable to the computer.

In the pulsed data transfer mode, the problem of constant "jitter" of the cornea is addressed. To obtain correct data, imaged moire patterns must be frozen by pulsing the illumination laser diode. The pulsed laser must be synchronized with the scanning rate of the TV camera and also the A/D conversion time of the frame grabber. When an operator turns on the keratometer system to start a data transfer sequence, the illuminating diode laser is temporarily shut off to clear the TV camera for at least 1/30 second. This eliminates a retained "ghost" image remaining from the previous illumination period. The diode laser then emits a synchronized pulse to generate an instantaneous moire pattern on the television screen by virtue of the novel optical system. On the next period of TV frame scanning the digitized information stored in the frame grabber is transferred to the computer at a slow rate by serial or parallel data transfer. The stored digitized information represents an original moire pattern imaged by the television camera. A software subrouthim program operates on the digital information moire patterns. A contour map and isometric three dimensional plot of the cornea is also possible as a computer readout.

Figure 4:
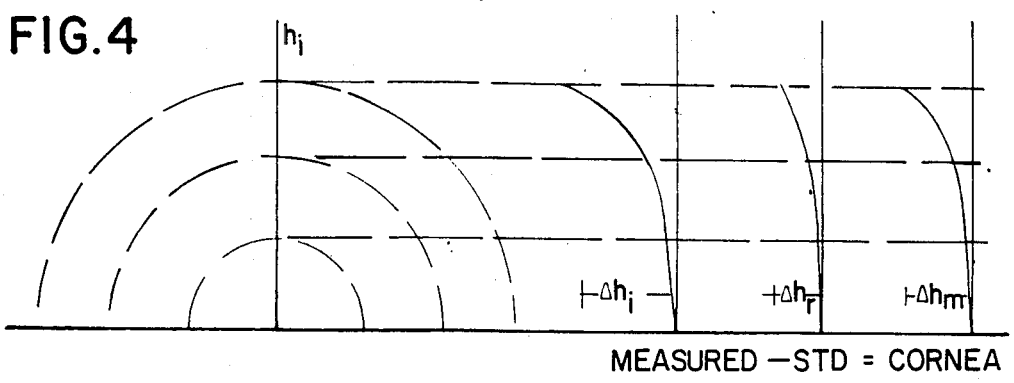
FIG. 4 shows data processing relationships.

The basic algorithim for moire fringe analysis involves the following steps with reference to FIG. 4.
  plotting in memory the $h_i$ vs. $\Delta h_r$ transverse aberration curve along an azimuth for a standard curvature calibration sphere simulating a cornea in place in the keratometer;
  plotting in memory the measured transverse aberration $h_i$ vs $\Delta h_i$ curve with a cornea in place, noting the position of moire fringes on the azimuth;
  subtracting the standard values from the measured values along the azimuths to obtain the cornea's effect, i.e. the curvature of the cornea which manifests itself as a transverse aberration;
  repeating the first three steps for each of eight azimuths displaced each 45° as shown in FIG. 3 to derive the aberration due to the cornea over 360° degrees of the moire image, and computing radius & power.

Figure 5:
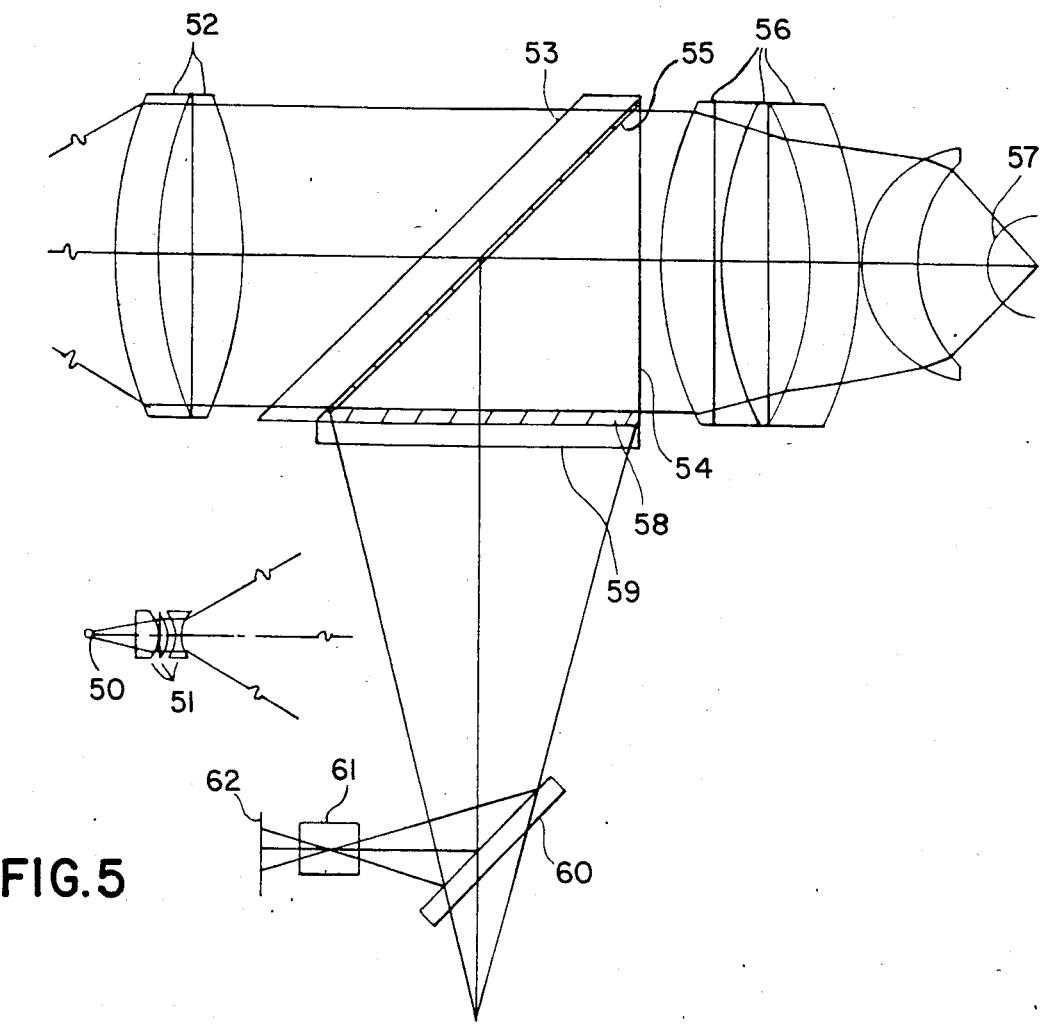
FIG. 5 shows a second embodiment of the invention in which a beam splitter reticle arrangement is used.

FIG. 5 shows a second embodiment of the invention.

Because the converging beam to the cornea is well corrected for spherical aberration, the spherical wave front is directed to the center of curvature of the cornea. The height of beam entrance to the lens is linear with the converging angle, and therefore to N.A.

If the circular grating is located at the entrance of the lens, and is illuminated by a perfectly collimated beam, the circular grating is demagnified at the cornea by the ratio of r/f. where r is a radius of curvature of the cornea, and f is the focal length of the converging lens. As an example, r=7.5 mm, f=37.5 mm. The ratio is 1/5. Thus a 5 times coarser plane grating is sufficient to accomplish fine grating projection to the cornea.

The return beam creates moire fringes with the entering collimated beam and these are recorded on the CCD camera at the proper demagnification.

In a third embodiment, the beam splitter 11 (FIG. 1) surface carries an elliptical concentric grating 55 (FIG. 5). Its projection to the converging lens 56 entrance pupil is a circular grating. The grating consists of equal transparent portions and opaque portions, the latter portions must have a highly reflective surface. The return beam from a spherical cornea will pass through the transparent zones, thus very high contrast moire fringes result since only light from deviating corneal areas will reach the imager.

Referring to FIG. 5, the beam from the diode 50 and optics 51 projected by collimating lens 52 and beamsplitter 53 is reflected at the cornea surface 57, and returns through lens 56, and then through circular grating 54 or elliptical grating 55. At the plane 58, bright moire fringes of high contrast are formed in a dark field.

The light reaching plane 58 may contain high frequency information from the gratings. This would contribute noise on the video signal and must be removed by a low pass optical filter which rejects the high frequencies while passing the wanted moire fringes. Such filtration can occur in fiber optics plates, etched surfaces, and ground glass and beaded screen, which are all useful embodiments.

In order to observe moire fringes with a C.C.D. camera lens, a Fresnel lens or plano convex lens 59, is located such that it converges the beam to demagnifying Lens 61, through surface reflection mirror 60.

Thus, the second embodiment is a simplified version of the first, having cost advantages thereover in terms of the optical implementation. The data processing will be the same for all embodiments.

While the preferred embodiments of the present invention have been described hereinabove, it is intended that all matter contained in the above description and shown in the accompanying drawings be interpreted as illustrative and not in a limiting sense and that all modification, constructions, and arrangements that fall within the scope and spirit of the invention be considered as having been made.

What is claimed is:
1. A method for real-time analysis of corneal curvature by measurement of aberration in a fiducial line image reflected from the corneal surface, comprising the steps of:
    projecting a polarized electromagnetic radiated fiducial line image on said corneal surface, which reflects said projected image;

separating said reflected image from said projected image by shifting the plane of polarization of said reflected image with respect to said projected image to produce a polarization shifted reflected image having information of curvature of said corneal surface;

superimposing a replica of said projected polarized fiducial line image on said polarization shifted reflected image, concentric therewith, to produce a composite moire image, including fringes and background;

detecting the moire image including fringes created by said superimposing step, and filtering said moire fringes from said background;

digitizing said filtered moire image for computing;

computing the number, and distance between said moire fringes to indicate the transverse aberration of said polarization shifted reflected image from said replica of said projected fiducial line image; and displaying the computed distances for interpretation of said corneal curvature, in real-time.

2. A method for real-time analysis of corneal curvature as described in claim 1 wherein said step of computing the distance between said moire fringes to indicate the transverse aberration of said polarization shifted reflected image from said replica of said projected fiducial line image, is performed over a plurality of azimuths and at a plurality of fixation points, whereby extended topography of the eye is obtained.

3. A real-time keratometer system for measuring the curvature of the cornea of the eye, which comprises:

illumination means having a planar wavefront;

means for projecting a pattern of fiducial lines on the cornea to reflect said pattern in accordance with the curvature of the cornea receiving illumination from said illumination means;

means for separating said projected fiducial line pattern from said reflected pattern, having an output beam containing said reflected pattern;

a reference fiducial line pattern reticle in concentric alignment with said reflected pattern in said output beam;

detector means adapted to receive said reflected pattern and said reference fiducial line pattern to detect transverse aberration of said reflected pattern from said reference pattern to form a difference image;

data processing means having an output for converting said difference image to digital numbers and computing the transverse aberration in said reflected pattern with respect to said reference pattern, and computing corneal radius and refractive power; and display means for displaying said data at said output of said data processing means.

4. A real-time keratometer system as described in claim 3 wherein said illumination means further comprises: a laser diode emitting a light beam in the infrared region of the electromagnetic spectrum and the inherent energy distribution is changed from Gaussian to uniform by an optical system consisting of a first lens having an undercorrected spherical aberration and a second lens which directs the uniform energy distribution to a planar wavefront.

5. A real-time keratometer system as described in claim 3 wherein said illumination means comprises: a laser diode having power terminals; and a pulsed power supply connected to said terminals, whereby the cornea is illuminated at a pulsed rate enabling natural constant movement of the eye to be eliminated from measurement data.

6. A keratometer as described in claim 3 wherein said means for separating said projected pattern of fiducial lines from said reflected pattern of fiducial lines is a linearly polarized prismodial beam splitter in combination with a quarter wave plate, whereby the reflected pattern is rotated 90 degrees from the projected pattern and reflected orthogonally by the beam splitter polarized surface preventing retracing of the reflected pattern back to the light source.

7. A real-time keratometer system as described in claim 3 wherein said detector means comprises:

a plurality of optical fibers having a finite length and a finite diameter, contiguous along their length, forming a multiaperture lens at one end and a substantially flat screen at the other end, said multiapertured lens having a fiducial line pattern thereon and having a curvature that is the conjugate of an optically perfect surface of a cornea whereby said multiapertured lens filters out background when said reflected beam is projected onto said multiapertured lens fiducial line pattern, concentrically therewith, and the filtered moire pattern is detected on said substantially flat screen end.

8. A real-time keratometer as described in claim 3 wherein said illumination means emits radiation in the visible electromagnetic spectrum.

9. A real-time keratometer system for measuring corneal curvature of the eye, which comprises:

an illumination source comprising a diode infrared laser and a Gaussian-to-uniformly illuminated planar wavefront light flux distribution lens providing a circularly uniform output beam;

optical lens means for collimating the planar light flux beam, said lens means having a conjugate curvature to a normal eye;

a first reticle having a fiducial line pattern thereon in the path of said planar light beam;

lens means for focusing said planar beam on a cornea, said lens means also adapted to collimate light flux reflected from the cornea in a reflected beam containing said fiducial line pattern modified from the projected beam fiducial line pattern in accordance with the curvature of the cornea;

a quarter wave plate for shifting the plane of polarization of the reflected beam;

a polarizing beam splitter receiving the reflected beam rotated 90 degrees by said quarter wave plate, adapted to orientate said reflected beam orthogonal to said projected beam;

a demagnifying lens receiving said reflected beam through said quarter wave plate and said beam splitter and having an output beam;

an optical detector receiving said output beam from said demagnifying lens, said detector having a scattering surface and a reference reticle thereon, said reticle being identical to said first reticle, said optical detector adapted to develop a moire pattern on its surface from the combination of said reflected beam from said beamsplitter and said reference reticle; said optical detector being adapted to filter out moire background, leaving only low frequency components for analysis;

a real-time analysis system including a display, receiving said moire pattern, digitizing it and computing the distances between fringes of said moire pattern along a plurality of azimuths thereof;

whereby the difference in distances between fringes along any azimuth indicates transverse aberration and said distances measured at a plurality of fixation points indicates corneal and limbus topography and areas having greatest curvature, and the information is displayed in real-time.

10. A realtime keratometer, which comprises:

a laser diode illumination means having a collimated beam;

a demagnifying lens having an entrance end and an exit end receiving said collimated beam at the entrance end;

a circular grating located at the entrance end of said demagnifying lens, projecting a demagnified circular grating image at the exit end of said demagnifying lens;

a beam splitter, adapted to receive light from the exit end of said demagnifying lens and direct said light therethrough, and direct reflected light angularly to said received light, whereby said reflected light demagnified image creates a moire pattern with said circular grating;

camera means for detecting said moire pattern and converting to electrical signals indicating moire fringes;

computer means receiving said electrical signals from said camera means adapted to compute curvature of the cornea from the distance between moire fringes along a plurality of azimuths, in real-time.

* * * * *